(12) United States Patent
Winslow et al.

(10) Patent No.: US 8,721,728 B2
(45) Date of Patent: May 13, 2014

(54) MODULAR GLENOID PROSTHESIS

(75) Inventors: Nathan A. Winslow, Warsaw, IN (US);
Clinton E. Kehres, Pierceton, IN (US);
Benjamin I. Joseph, Ft. Wayne, IN (US); Bryce A. Isch, Bluffton, IN (US);
Russell F. Warren, Greenwich, CT (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/447,627

(22) Filed: Apr. 16, 2012

(65) Prior Publication Data
US 2012/0277880 A1 Nov. 1, 2012

Related U.S. Application Data

(60) Provisional application No. 61/479,622, filed on Apr. 27, 2011.

(51) Int. Cl.
*A61F 2/40* (2006.01)

(52) U.S. Cl.
USPC .................................... 623/19.13; 623/19.12

(58) Field of Classification Search
USPC ........................................... 623/19.11–19.14
See application file for complete search history.

(56) References Cited

U.S. PATENT DOCUMENTS

| | | | |
|---|---|---|---|
| 2005/0010300 A1* | 1/2005 | Disilvestro et al. | 623/18.12 |
| 2005/0261775 A1 | 11/2005 | Baum et al. | |
| 2006/0020344 A1* | 1/2006 | Shultz et al. | 623/19.12 |
| 2006/0200248 A1* | 9/2006 | Beguin et al. | 623/19.11 |
| 2007/0100458 A1* | 5/2007 | Dalla Pria | 623/19.13 |
| 2007/0244563 A1* | 10/2007 | Roche et al. | 623/19.12 |
| 2008/0228281 A1* | 9/2008 | Forrer et al. | 623/19.12 |
| 2008/0294268 A1 | 11/2008 | Baum et al. | |
| 2009/0164021 A1* | 6/2009 | Dallmann | 623/19.11 |

FOREIGN PATENT DOCUMENTS

| | | |
|---|---|---|
| EP | 1639967 A1 | 3/2006 |
| EP | 1782764 A2 | 5/2007 |

OTHER PUBLICATIONS

Biomet Orthopedics, Comprehensive Shoulder System, Surgical Technique, pp. 1-53 (2007).
Biomet Orthopedics, Comprehensive Reverse Shoulder System, Surgical Technique, pp. 1-39 (2009).
Partial International Search Report for PCT/US2012/034093 (in English) mailed Jun. 14, 2012; ISA/EP.

* cited by examiner

*Primary Examiner* — Marcia Hoffman
(74) *Attorney, Agent, or Firm* — Harness, Dickey

(57) ABSTRACT

The present teachings provide a modular glenoid prosthesis for replacing a portion of the anatomy. The prosthesis can comprise a platform having a coupling portion, a base and a central bore that extends from the coupling portion through the base. The central bore can define a tapered region, and the coupling portion can include a plurality of bores and a groove coupling feature. The prosthesis can include a glenoid component having a plurality of pegs. Each of the plurality of pegs in combination with at least one tab, the tab configured to engage the groove coupling feature of the platform can be coupled to a respective one of the plurality of bores. The prosthesis can include a glenosphere including a tapered stem couplable to the tapered region. The glenoid component and the glenosphere are selectively couplable to the platform for replacing the portion of the anatomy.

16 Claims, 6 Drawing Sheets

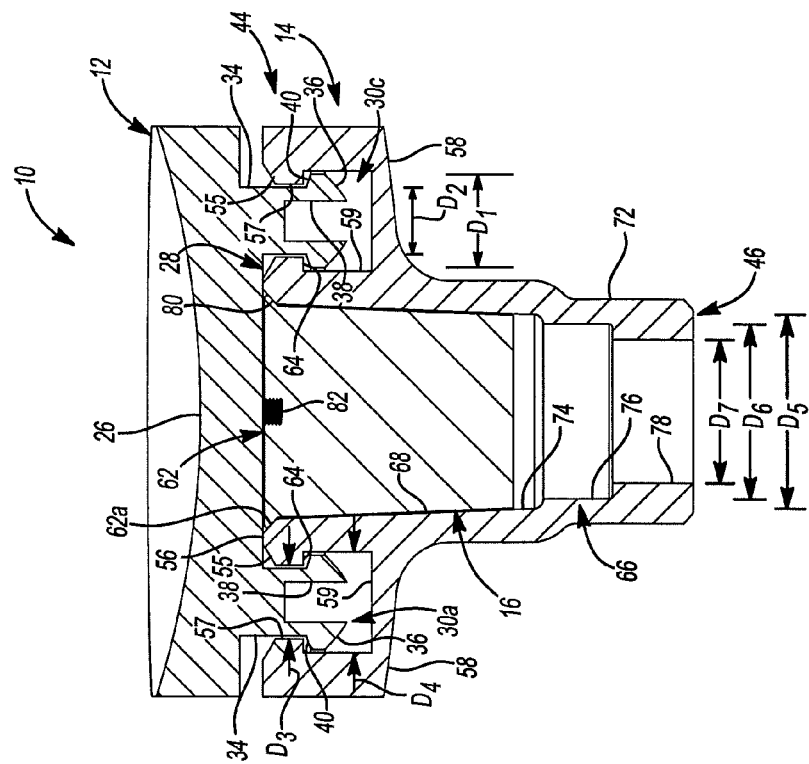

_US 8,721,728 B2_

MODULAR GLENOID PROSTHESIS

CROSS-REFERENCE TO RELATED APPLICATIONS

This application claims the benefit of U.S. Provisional Application No. 61/479,622, filed on Apr. 27, 2011. The entire disclosure of the above application is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function or repair the damaged tissue. Surgical intervention can include any surgical procedure that can restore function to the damaged tissue, which can require the use of one or more orthopedic prostheses, such as orthopedic nails, screws, implants, etc., to restore function to the damaged tissue.

The present disclosure relates to a prosthesis for use in restoring function to damaged tissue, and more specifically relates to a modular glenoid prosthesis.

SUMMARY

According to various aspects, provided is a modular glenoid prosthesis for replacing a portion of the anatomy. The prosthesis can comprise a platform having a coupling portion, a base and a central bore that extends from the coupling portion through the base. The central bore can define a tapered region, and the coupling portion can include a plurality of bores. The prosthesis can include a glenoid component having a plurality of pegs. Each of the plurality of pegs can be coupled to a respective one of the plurality of bores. The prosthesis can include a glenosphere having a tapered stem couplable to the tapered region. The glenoid component and the glenosphere are selectively couplable to the platform for replacing the portion of the anatomy.

Additionally provided is a modular glenoid prosthesis for replacing a portion of the anatomy. The prosthesis can comprise a platform having a plurality of sides, a coupling portion and a central bore defining a tapered region. The coupling portion can include a plurality of bores, and at least one of the plurality of sides can include a coupling feature. The prosthesis can include a glenoid component having a plurality of pegs and at least one augment. Each of the plurality of pegs can be coupled to a respective one of the plurality of bores so that the at least one augment engages the coupling feature. The at least one augment can be formed on the glenoid component such that when the glenoid component is coupled to the platform, the augment is at or below a surface of the platform.

Further provided is a method of using a modular glenoid prosthesis to replace a portion of the anatomy. The method can include coupling a platform having a coupling portion that defines a plurality of bores and a central bore that includes a tapered region to a glenoid cavity. The method can also include performing either a first procedure or a second procedure. The first procedure can include inserting a taper plug into the central bore and coupling a glenoid component having a plurality of pegs to the plurality of bores. The second procedure can include coupling a glenosphere having a taper to the tapered region of the center bore so that the taper and the tapered region lock to couple the glenosphere to the platform.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 2 is an exploded view of the modular glenoid prosthesis of FIG. 1;

FIG. 3 is a cross-sectional view of the modular glenoid prosthesis of FIG. 1, taken along line 3-3 of FIG. 1;

DESCRIPTION OF VARIOUS ASPECTS

Figure 1:
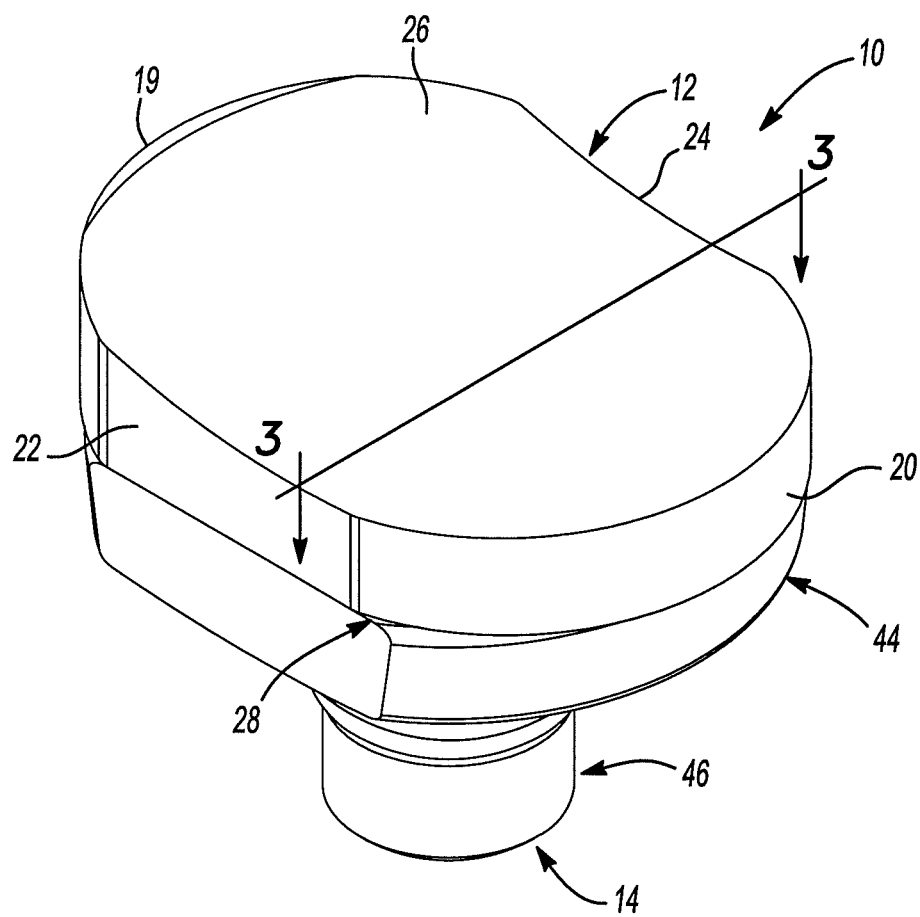
FIG. 1 is a perspective view an exemplary modular glenoid prosthesis according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a system for use in an anatomy to restore function to damaged tissue, such as in the case of a shoulder joint, it will be understood that the teachings of the prosthesis as described and claimed herein can be used in any appropriate surgical procedure. Therefore, it will be understood that the following discussions are not intended to limit the scope of the present teachings and claims herein.

Figure 4:
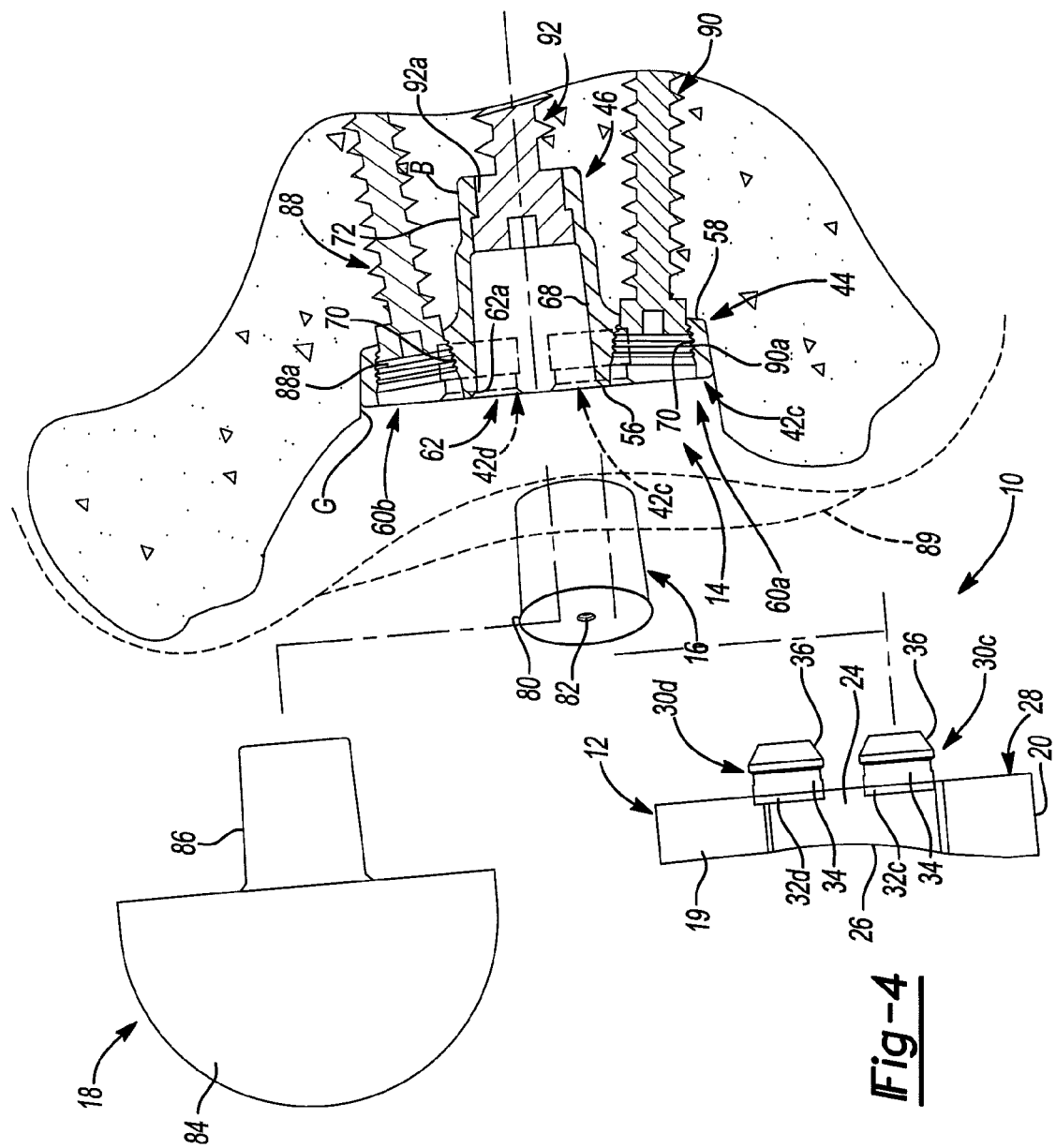
FIG. 4 is a schematic environmental illustration of the modular glenoid prosthesis of FIG. 1 being used to perform either an anatomic shoulder procedure or a reverse shoulder procedure.

With reference to FIGS. 1-4, a modular glenoid prosthesis 10 is shown. The modular glenoid prosthesis 10 may be particularly adapted for a total shoulder replacement (FIG. 4). Various aspects of the present teachings, however, may have application for other procedures. In certain applications, as will be discussed further herein, the modular glenoid prosthesis 10 can be used with both an anatomic replacement and a reverse shoulder replacement. This flexibility can enable the surgeon to perform an anatomical replacement, and then easily perform a reverse shoulder in the event the patient's condition worsens. With reference to FIGS. 1-4, the modular glenoid prosthesis 10 can include a glenoid component 12, a base plate or platform 14, a taper plug 16 and a glenosphere 18 (shown particularly in FIG. 4).

The glenoid component 12 can be coupled to the platform 14 to articulate with a humeral head. The glenoid component 12 can be composed of any suitable biocompatible material, such as a biocompatible metal or polymer. For example, the glenoid component 12 can be composed of a polyether ether ketone (PEEK). With particular reference to FIGS. 1 and 2, the glenoid component 12 can have a first arcuate side 19 substantially opposite a second arcuate side 20 and a first planar side 22 opposite a second planar side 24. The first arcuate side 19, second arcuate side 20, first planar side 22 and second planar side 24 can enable the shape of the glenoid component 12 to generally conform to a glenoid cavity of the patient. The glenoid component 12 can also include a first or an articulating surface 26 opposite a second or a coupling surface 28.

With particular reference to FIGS. 2, and 3, the articulating surface 26 can be substantially concave to enable articulation with a humeral head. The coupling surface 28 can include at least one glenoid peg 30 and at least one relief 32. In one example, the coupling surface 28 can include four glenoid pegs 30a-30d, however, any number of glenoid pegs 30 could be employed. Generally, the glenoid pegs 30a-30d can be integrally formed with the coupling surface 28, however, the glenoid pegs 30a-30d could be discretely formed and coupled to the coupling surface 28 via any suitable technique, such as mechanical fasteners, adhesives or through a post processing step. The glenoid pegs 30a-30d can be coupled to the coupling surface 28 so as to be symmetrical with respect to a longitudinal axis L of the glenoid component 12. Alternatively, the glenoid pegs 30a-30d can be arranged on the coupling surface 28 in any desired fashion to couple the glenoid component 12 to the platform 14.

In one example, as best shown in FIG. 3, each glenoid peg 30a-30d can include a stem 34, a conical tip 36 and a slot 38. The stem 34 can be substantially cylindrical and can be coupled to the coupling surface 28 and the conical tip 36. The conical tip 36 can couple each of the glenoid pegs 30a-30d to the platform 14. For example, the conical tip 36 can include a lip 40. The lip 40 can be formed adjacent to the stem 34 and can cooperate with the platform 14 to removably couple the glenoid component 12 to the platform 14, as will be discussed herein. The slot 38 can extend through the conical tip 36 to a portion of the stem 34. The slot 38 can enable the glenoid pegs 30a-30d to snap into the platform 14, as will be discussed herein. In this regard, the lip 40 of the conical tip 36 can have a diameter D1, which can be greater than a diameter D2 of a portion of the at least one bore 42 of the platform 14. The slot 38 can enable the conical tip 36 to be compressed into a smaller diameter, so that the glenoid pegs 30a-30d can be received within the at least one bore 42.

With reference to FIGS. 2 and 3, the at least one relief 32 can be formed adjacent to each of the at least one glenoid peg 30. Thus, in this example, four reliefs 32a-32d can be formed adjacent to the four glenoid pegs 30a-30d. The reliefs 32a-32d can comprise cut-outs or portions of the coupling surface 28 with a reduced thickness. The reliefs 32a-32d can be sized to enable an instrument, such as an osteotome, to be positioned between the glenoid component 12 and the platform 14 to remove the glenoid component 12 from the platform 14 when the glenoid component 12 is coupled to the platform 14.

Referring to FIGS. 1-3, the platform 14 can include a coupling portion 44 and a base 46. Generally, the coupling portion 44 can be integrally formed with the base 46, however, the coupling portion 44 and the base 46 could each be discretely formed and coupled together via any suitable technique, such as mechanical fasteners, adhesives, welding or through a post processing step. The platform 14 can be composed of any suitable biocompatible material, such as a biocompatible metal or polymer. For example, the platform 14 can be composed of titanium. In addition, the platform 14 can be coated with a biocompatible material to facilitate bone in-growth. Exemplary biocompatible materials include a porous metal matrix, such as a porous plasma spray, calcium phosphate, which can include hydroxyapatite, a biologically active substance, such as a bone morphogenic protein, a growth factor, a peptide, antibiotic, etc.

With reference to FIGS. 2 and 3, the coupling portion 44 can have a first arcuate side 48 substantially opposite a second arcuate side 50 and a first planar side 52 opposite a second planar side 54. As with the shape of the glenoid component 12, the first arcuate side 48, second arcuate side 50, first planar side 52 and second planar side 54 can enable the shape of the coupling portion 44 to generally conform to a glenoid cavity of the patient. The shape of the coupling portion 44 can also correspond to the shape of the glenoid component 12, however, it should be understood that the glenoid component 12 could have varying shapes and sizes if desired to correspond with the patient's anatomy.

The coupling portion 44 can also include the at least one bore 42, a first surface 56, a second surface 58, at least one coupling bore 60 and a central bore 62. The first surface 56 and the second surface 58 can be substantially planar. The at least one bore 42 can be formed through the first surface 56, but can be formed so as to not extend through the second surface 58. In one example, the at least one bore 42 can comprise four bores 42a-42d. The bores 42a-42d can be formed through the first surface 56 and can be arranged about the first surface 56 such that the bores 42a-42d are substantially symmetrical with respect to a longitudinal axis L1 of the platform 14. In one example, the bores 42a-42d can be positioned in pairs of bores 42a, 42b; 42c, 42d adjacent to a respective one of the first planar side 52 and the second planar side 54. Generally, the bores 42a-42d can be positioned so that each one of the glenoid pegs 30a-30d can be snap-fit into each one of the bores 42a-42d to couple the glenoid component 12 to the platform 14.

With reference to FIG. 3, each of the bores 42a-42d can include a chamfered edge 55, an entry portion 57 with a diameter D3 having a first dimension and a retaining portion 59 with a diameter D4 having a second dimension. The chamfered edge 55 can provide a guide for directing the glenoid pegs 30a-30d into the bores 42a-42d. The diameter D3 can be smaller than a diameter D4 so as to form an abutment 64. The abutment 64 can contact the lip 40 of the glenoid pegs 30a-30d to removably couple the glenoid pegs 30a-30d to the bores 42a-42d.

The at least one coupling bore 60 can receive a suitable fastening device to couple the platform 14 to the anatomy, as will be discussed in greater detail herein. In one example, the at least one coupling bore 60 can comprise two coupling bores 60a, 60b, which can each extend from the first surface 56 through the second surface 58. Each of the coupling bores 60a, 60b can be positioned about the longitudinal axis L1 of the platform 14 such that a centerline C of each of the coupling bores 60a, 60b can substantially intersect the longitudinal axis L1 of the platform 14. Generally, each of the coupling bores 60a, 60b can be positioned adjacent to a respective one of the first arcuate side 48 and the second arcuate side 50. The coupling bores 60a, 60b can optionally include a plurality of threads 70 formed adjacent to the second surface 58. The plurality of threads 70 can cooperate with a suitable fastener to secure the platform 14 to the anatomy, as will be discussed in greater detail herein. It should be noted that although the coupling bores 60a, 60b are described and illustrated herein as comprising the plurality of threads 70, one or both of the coupling bores 60a, 60b can be unthreaded.

With reference to FIGS. 2 and 3, the coupling bores 60a, 60b and the bores 42a-42d can be formed around the central bore 62. The central bore 62 can be defined from the first surface 56 to the second surface 58. The central bore 62 can include a chamfered edge 62a. The chamfered edge 62a can contact a portion of the taper plug 16 to support the taper plug 16 when the taper plug 16 is positioned within the platform 14

(FIG. 3). The central bore 62 can be coaxially aligned with a center bore 66 of the base 46. The central bore 62 of the coupling portion 44 and the center bore 66 of the base 46 can cooperate to define a central bore that extends from the coupling portion 44 through the base 46. The central bore 62 of the coupling portion 44 and the center bore 66 of the base 46 can also cooperate to define tapered region 68. The tapered region 68 can enable the glenosphere 18 to be coupled to the platform 14, as will be discussed herein. In one example, the tapered region 68 can comprise a Morse taper, which can cooperate with the glenosphere 18 to couple the glenosphere 18 to the platform 14 (FIG. 4). The central bore 62 of the coupling portion 44 and the center bore 66 of the base 46 can also cooperate to receive the taper plug 16, as will be discussed herein.

It should be noted that although the platform 14 is described and illustrated herein as comprising coupling bores 60a, 60b and central bore 62 for securing the platform 14 to the anatomy, any other suitable technique could be used to couple the platform 14 to the anatomy. For example, one or more pegs could be coupled to the second surface 58 of the coupling portion 44 and used to secure the platform 14 in the anatomy. The one or more pegs could be used in combination with the coupling bores 60a, 60b and the central bore 62. The one or more pegs could be cemented or uncemented. In addition or in the alternative, the platform 14 could include a protrusion extending outwardly from the center bore 66 of the base 46, which could be coated with a biocompatible material to facilitate bone in-growth to secure the platform 14 in the glenoid cavity.

With reference to FIGS. 2 and 3, the base 46 can be coupled to or extend outwardly from the second surface 58 of the coupling portion 44. The base 46 can be substantially cylindrical, and can include a tapered or stepped exterior surface 72. Generally, the exterior surface 72 can be shaped so as to facilitate insertion of the base 46 into the anatomy, and thus, can include a reduced diameter leading end and a larger diameter trailing end, as illustrated. It should be noted, however, that the base 46 can have any desired shape for insertion into the anatomy. The base 46 can include the center bore 66. The center bore 66 can extend through the base 46. In one example, the center bore 66 can have a first portion 74, a second portion 76 and a third portion 78.

The first portion 74 can have a diameter D5, which can cooperate with the central bore 62 to define the tapered region 68. The second portion 76 can have a diameter D6, which can be smaller than the diameter D5, but larger than a diameter D7 of the third portion 78. As will be discussed in greater detail herein, the second portion 76 and the third portion 78 can receive a portion of a fastening device therein to aid in coupling the base 46 to the anatomy, if desired.

The taper plug 16 can be received within the first surface 56 of the coupling portion 44 and the first portion 74 of the base 46 when the glenoid component 12 is coupled to the platform 14. The taper plug 16 can be composed of any suitable biocompatible material, such as a biocompatible metal or polymer. For example, the taper plug 16 can be composed of titanium.

The use of a metal taper plug 16 can reduce the likelihood for a polymeric glenoid component 12 to creep into the central bore 62. The taper plug 16 can also support and distribute a load received from the glenoid component 12. The taper plug 16 can be generally cylindrical, and can include a lip 80. The lip 80 can cooperate with the chamfered edge 62a of the central bore 62 to support the taper plug 16 within the central bore 62 and center bore 66. Generally, the taper plug 16 rests on the chamfered edge 62a and does not lock into the tapered region 68 of the central bore 62 and center bore 66. Optionally, the taper plug 16 can include a small threaded bore 82, which can be used to easily remove the taper plug 16 from the platform 14.

With reference to FIG. 4, the glenosphere 18 can be coupled to the platform 14 instead of the glenoid component 12 in a reverse shoulder procedure. In this regard, the platform 14 can enable the use of either the glenoid component 12 or the glenosphere 18, and can allow the glenoid component 12 to be removed so that a glenosphere 18 can be coupled to the platform 14. As the glenosphere 18 can be commercially available from Biomet Manufacturing Corporation of Warsaw, Ind., and can comprise, for example, a Versa-Dial® glenosphere, the glenosphere 18 will not be discussed in detail herein.

Briefly, however, the glenosphere 18 can include a head 84 and a tapered stem 86. The head 84 can be substantially hemispherical, and can be coupled to the tapered stem 86 through any suitable technique. For example, the head 84 can be directly coupled to the tapered stem 86 or can be coupled to the tapered stem 86 so as to be offset from the tapered stem 86, such as the Versa-Dial® glenosphere commercially available from Biomet Manufacturing Corporation of Warsaw, Ind. The tapered stem 86 can comprise a taper that locks with the tapered region 68 of the platform 14. In one example, the tapered stem 86 can comprise a Morse taper. The locking of the tapered stem 86 to the tapered region 68 of the platform 14 can couple the glenosphere 18 to the platform 14 in a reverse shoulder procedure.

The glenoid component 12, the platform 14, the taper plug 16 and the glenosphere 18 can be provided together as a surgical kit. Such a surgical kit can provide the surgeon with the flexibility to decide in the operating room whether to perform an anatomical shoulder procedure employing the glenoid component 12 and taper plug 16 with the platform 14 or a reverse shoulder procedure using the glenosphere 18 and the platform 14. Alternatively, the glenoid component 12, the platform 14 and the taper plug 16 can be provided separately, and the glenosphere 18 can be provided separately.

In order to couple the platform 14 to the anatomy, an incision 89 can be formed adjacent to the glenoid cavity G. Then, the glenoid cavity G can be prepared for receipt of the platform 14. In one example, a bore B can be formed in the glenoid cavity G, which can receive the base 46. Then, the platform 14 can be positioned on the glenoid cavity G so that the base 46 is received within the bore B. Next, the platform 14 can be secured to the glenoid cavity G in a variety of ways. In one example, a first bone screw 88 and a second bone screw 90 can be received within a respective one of the coupling bores 60a, 60b. If desired, the first bone screw 88 and second bone screw 90 can include threaded heads 88a, 90a, which can engage the plurality of threads 70 of the coupling bores 60a, 60b. It should be noted that the first bone screw 88 and the second bone screw 90 could have unthreaded heads if desired to aid in compression. Further, one of the first bone screw 88 and the second bone screw 90 could have a threaded head, while the other of the first bone screw 88 and the second bone screw 90 could have an unthreaded head. Thus, the use of the first bone screw 88 and second bone screw 90 is merely exemplary. The first bone screw 88 and the second bone screw 90 can aid in anti-rotation and pull out strength.

In one example, a third bone screw 92 can be inserted into the central bore 62 and the first surface 56 to further secure the platform 14 to the anatomy. The third bone screw 92 can be inserted into the platform 14 such that a head 92a of the third bone screw 92 can engage the second portion 76 and third portion 78 of the center bore 66. The third bone screw 92 can provide compression. It should be noted that while the head 92a of the third bone screw 92 is illustrated herein as being unthreaded, the head 92a and at least one of the second portion 76 and third portion 78 could include threads if desired.

Further, it will be understood that although the platform 14 is illustrated herein as being secured to the glenoid cavity G via the first bone screw 88, the second bone screw 90 and the third bone screw 92, the platform 14 could be secured to the anatomy via one or more pegs, as discussed previously herein. The pegs could be cemented or non-cemented to the anatomy. Further, any combination of pegs, cemented or non-cemented, and bone screws could be employed to secure the platform 14 to the anatomy.

With the platform 14 coupled to the glenoid cavity G, the surgeon can decide whether to perform an anatomic shoulder procedure or a reverse shoulder procedure. In one example, the surgeon can decide to perform an anatomic shoulder procedure, and can insert the taper plug 16 into the central bore 62 so that the lip 80 of the taper plug 16 engages the chamfered edge 62a of the central bore 62. Then, the glenoid component 12 can be coupled to the platform 14 such that the glenoid pegs 30a-30d are snapped into the bores 42a-42d of the coupling portion 44 of the platform 14.

Subsequently, if the surgeon decides that a reverse shoulder procedure should be performed, an osteotome can be inserted into the reliefs 32a-32d of the glenoid component 12 to separate the glenoid component 12 from the platform 14. Then, the taper plug 16 can be removed from the platform 14. In one example, a tool can engage the threaded bore 82 of the taper plug 16 to remove the taper plug 16 from the platform 14. The tapered stem 86 of the glenosphere 18 can be positioned within the platform 14 so that the tapered stem 86 frictionally locks with the tapered region 68 of the platform 14 to secure the glenosphere 18 to the platform 14.

Alternatively, if the surgeon desires to first perform a reverse shoulder procedure, with the platform 14 coupled to the anatomy, the tapered stem 86 of the glenosphere 18 can be positioned within the platform 14 so that the tapered stem 86 frictionally locks with the tapered region 68 of the platform 14 to secure the glenosphere 18 to the platform 14. Subsequently, if the surgeon decides that an anatomic shoulder procedure should be performed, the glenosphere 18 can be removed from the platform 14. Then, the taper plug 16 can be inserted into the central bore 62 so that the lip 80 of the taper plug 16 engages the chamfered edge 62a of the central bore 62. Then, the glenoid component 12 can be coupled to the platform 14 such that the glenoid pegs 30a-30d are snapped into the bores 42a-42d of the coupling portion 44 of the platform 14.

Thus, the platform 14 can enable a surgeon to perform an anatomic shoulder procedure or a reverse shoulder procedure by allowing either a glenoid component 12 or a glenosphere 18 to be coupled to the platform 14. This can allow a surgeon to remove the glenoid component 12 to perform a reverse shoulder procedure without requiring removal of the entire anatomic shoulder prosthesis, thereby decreasing the amount of bone removed to convert from an anatomic shoulder replacement to a reverse shoulder replacement. The ease of removing only a portion of the anatomic shoulder replacement to convert to a reverse shoulder replacement can also reduce surgical time, and lead to a faster patient recovery.

Figure 5:
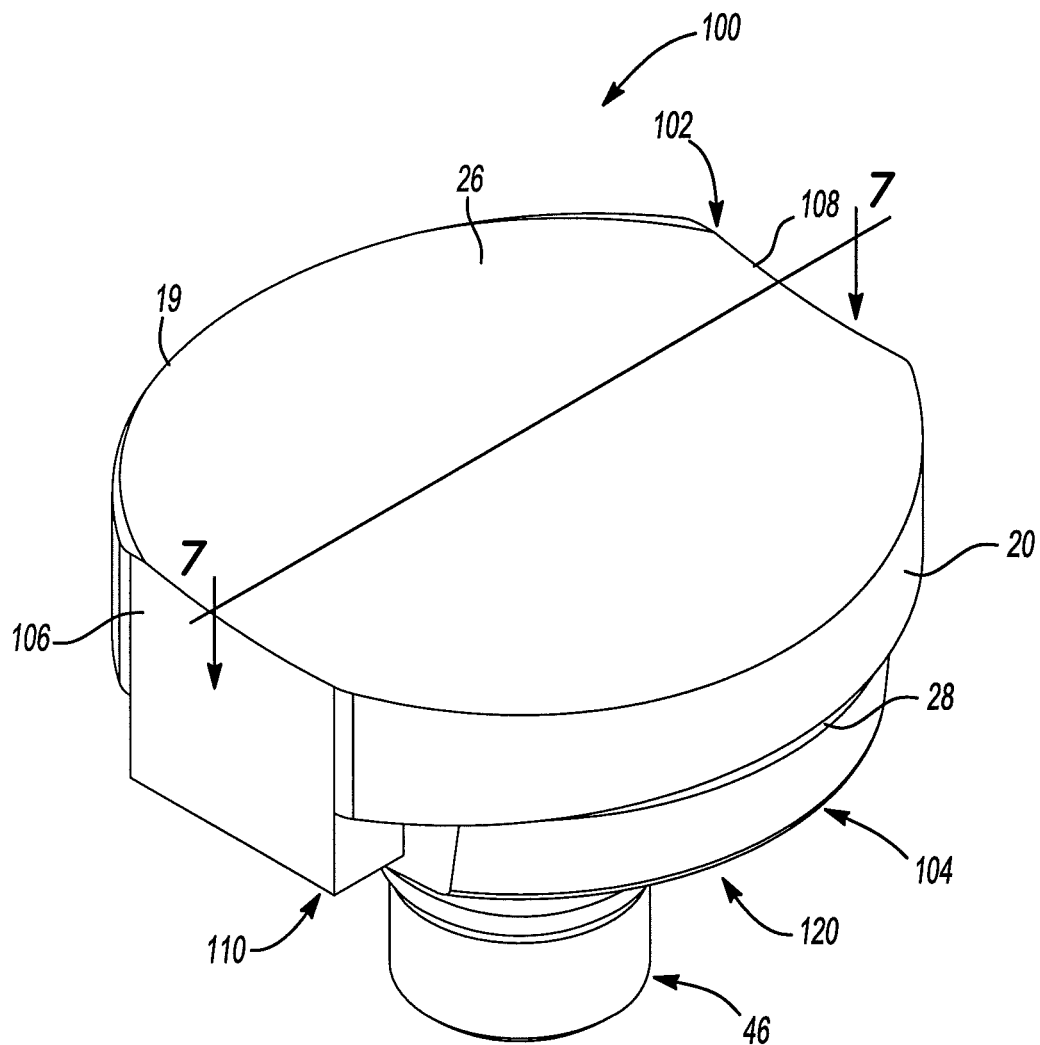
FIG. 5 is a perspective view of a portion of an exemplary modular glenoid prosthesis according to the present teachings.
Figure 6:
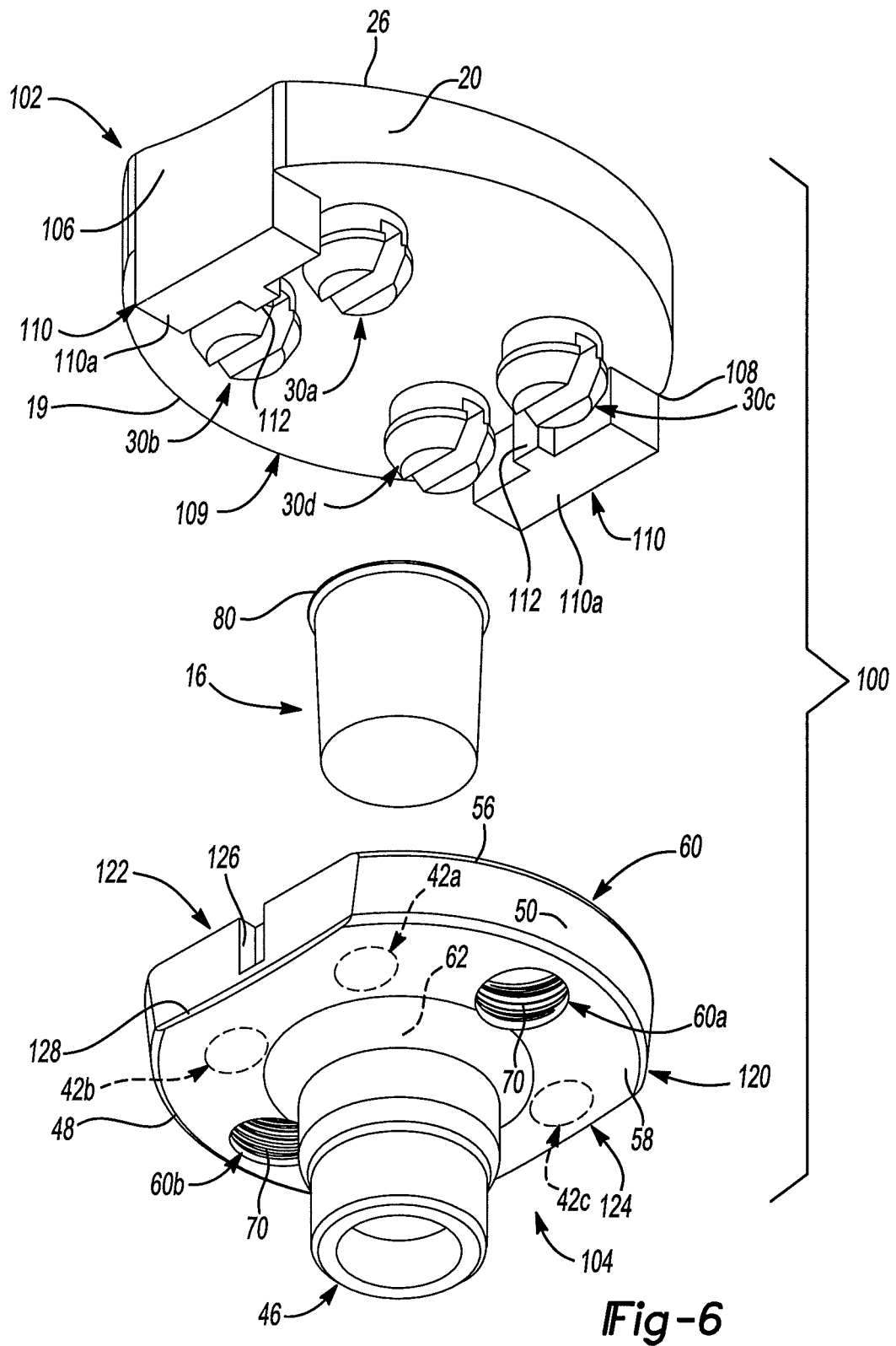
FIG. 6 is an exploded view of the modular glenoid prosthesis of FIG. 1.
Figure 7:
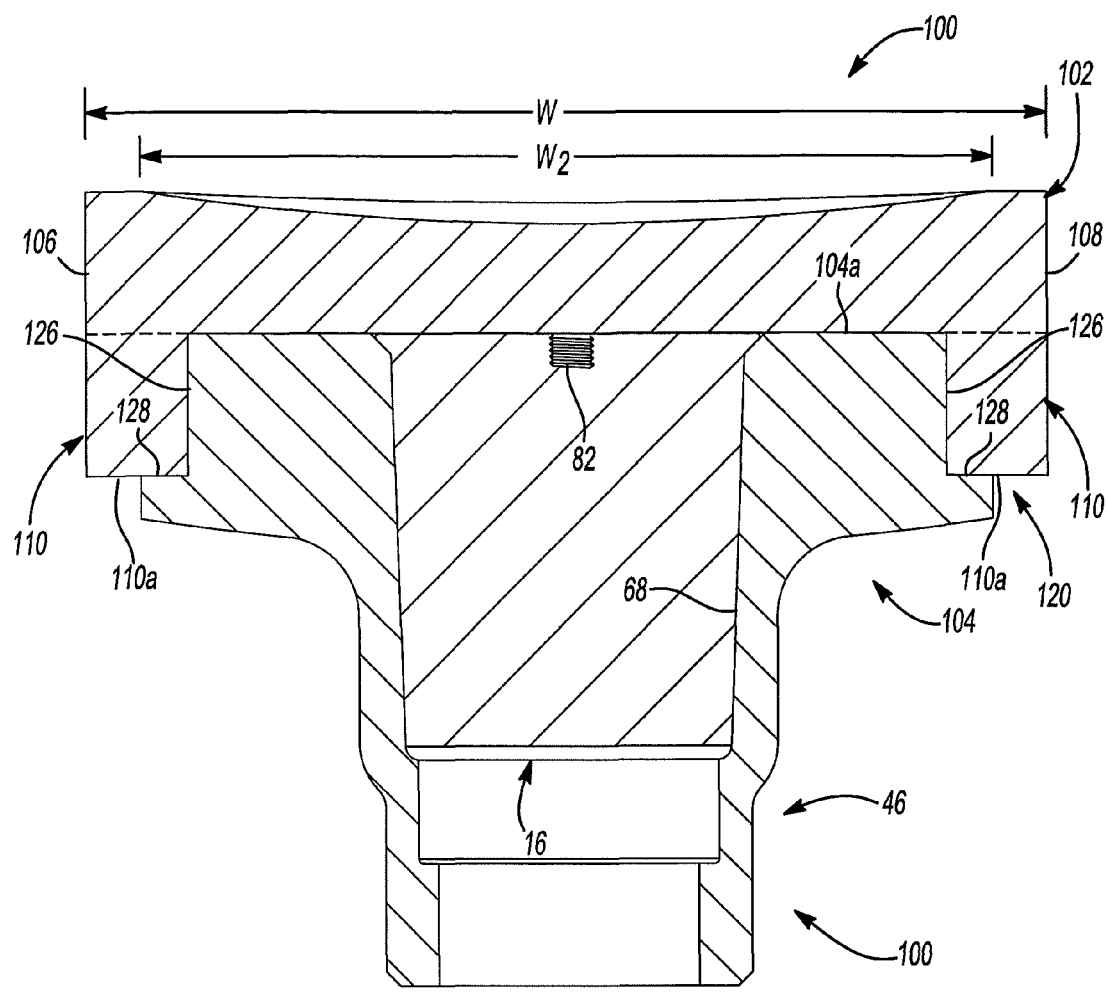
FIG. 7 is a cross-sectional view of the modular glenoid prosthesis of FIG. 5, taken along line 7-7 of FIG. 5.

With reference now to FIGS. 5-7, in one example, a modular glenoid prosthesis 100 can be employed to repair a damaged portion of an anatomy. As the modular glenoid prosthesis 100 can be similar to the modular glenoid prosthesis 10 described with reference to FIGS. 1-4, only the differences between the modular glenoid prosthesis 10 and the modular glenoid prosthesis 100 will be discussed in great detail herein, and the same reference numerals will be used to denote the same or similar components. With reference to FIGS. 5-7, the modular glenoid prosthesis 100 can include a glenoid component 102, a base plate or platform 104 and the taper plug 16, and can be used with the glenosphere 18 (FIG. 4).

The glenoid component 102 can be coupled to the platform 104 to articulate with a humeral head. The glenoid component 102 can be composed of any suitable biocompatible material, such as a biocompatible metal or polymer. For example, the glenoid component 102 can be composed of a polyether ether ketone (PEEK). With reference to FIGS. 5 and 6, the glenoid component 102 can have the first arcuate side 19 substantially opposite the second arcuate side 20 and a first planar side 106 opposite a second planar side 108. The first arcuate side 19, second arcuate side 20, first planar side 106 and second planar side 108 can enable the shape of the glenoid component 102 to conform to a glenoid cavity of the patient. The glenoid component 102 can also include the first or articulating surface 26 opposite a second or coupling surface 109. The coupling surface 109 can include the at least one glenoid peg 30, but generally does not include the at least one relief 32. The at least one relief 32, however, can be optional.

With reference to FIGS. 6 and 7, the first planar side 106 and the second planar side 108 can also include an augment 110. The augment 110 can be composed of any suitable biocompatible material, such as a biocompatible metal or polymer. For example, the augment 110 can comprise a metal, which can be molded with the polymeric glenoid component 102 such that the metal is substantially encapsulated within the polymeric glenoid component 102. Alternatively, the augment 110 could be molded separately and coupled to the glenoid component 102 via any suitable technique, such as mechanical fasteners, etc. Generally, the metal portion of the augment 110 can be coupled to the first planar side 106 and the second planar side 108 such that the augment 110 extends at or below an uppermost or first surface 104a of the platform 104 (FIG. 7). The augment 110 can include a tab 112, which can engage a portion of the platform 104. The tab 112 can be generally rectangular, however, the tab 112 can have any desired shape. The engagement between the tab 112 and the platform 104 can further couple the glenoid component 102 to the platform 104, while providing additional support for the augment 110 and in turn the larger glenoid component 102.

In this regard, the augment 110 can enable the use of the glenoid component 102, which is larger than the platform 104. In this example, with reference to FIG. 7, the glenoid component 102 can have a width W, which can be greater than a width W2 of the platform 104. The use of the augment 110 below the first planar side 106 and the second planar side 108 provides support for the larger size of the glenoid component 102, without requiring the use of a platform 104 with a greater width W2. This can enable the use of a single platform 104 with a variety of differently sized glenoid components 102. It should be understood, that although only the width W of the glenoid component 102 is illustrated herein as being larger than the width W2 of the platform 104, any portion of the glenoid component 102 can be sized larger than the platform 104 depending upon the particular patient. Thus, if desired, an augment 110 can be formed under one or more of the first arcuate surface 19, second arcuate surface 20, etc. to enable a single platform 104 to be used with the variety of differently sized glenoid components 102. Further, it should be understood that the use of the augment 110 is merely exemplary, as if desired, various sizes of platforms 14, 104 could be employed to match glenoid components 12, 102 of various sizes.

Referring to FIGS. 6 and 7, the platform 104 can include a coupling portion 120 and the base 46. Generally, the coupling portion 120 can be integrally formed with the base 46, however, the coupling portion 120 and the base 46 could each be discretely formed and coupled together via any suitable technique, such as mechanical fasteners, adhesives, welding or through a post processing step. The platform 104 can be composed of any suitable biocompatible material, such as a biocompatible metal or polymer. For example, the platform 104 can be composed of titanium. In addition, the platform 104 can be coated with a biocompatible material to facilitate boney in-growth, such as a porous metal matrix, such as a porous plasma spray, calcium phosphate, which can include hydroxyapatite, a biologically active substance, such as a bone morphogenic protein, a growth factor, a peptide, antibiotic, etc.

With reference to FIGS. 6 and 7, the coupling portion 120 can have the first arcuate side 48 substantially opposite the second arcuate side 50 and a first planar side 122 opposite a second planar side 124. The first arcuate side 48, second arcuate side 50, first planar side 122 and second planar side 124 can enable the shape of the coupling portion 120 to conform to a glenoid cavity of the patient. The coupling portion 120 can also include the at least one bore 42, the first surface 56, the second surface 58, the at least one coupling bore 60 and the central bore 62. The first planar side 122 and second planar side 124 can be configured to support the augment 110.

In one example, the first planar side 122 and second planar side 124 can include a coupling feature for mating with the augment 110, such as a groove 126 and a lip 128. The groove 126 can be configured to receive the tab 112. The engagement of the tab 112 with the groove 126 can further resist rotation of the glenoid component 102 relative to the platform 104. The lip 128 can be formed along each of the first planar side 122 and second planar side 124 and can extend outwardly to support at least a portion of the augment 110. The contact between the lip 128 and the augment 110 can also allow for a transfer of forces from the augment 110 to the platform 104.

The glenoid component 102, the platform 104, the taper plug 16 and the glenosphere 18 can be provided together as a surgical kit. Such a kit can provide the surgeon with the flexibility to decide in the operating room whether to perform an anatomical shoulder procedure employing the glenoid component 102 and taper plug 16 with the platform 104 or a reverse shoulder procedure using the glenosphere 18 and the platform 104. Alternatively, the glenoid component 102, the platform 104 and the taper plug 16 can be provided separately, and the glenosphere 18 can be provided separately.

As the surgical insertion of the modular glenoid prosthesis 100 can be similar to the surgical insertion and insertion of the modular glenoid prosthesis 10, the surgical insertion of the modular glenoid prosthesis 100 will not be discussed in great detail herein. Briefly, however, with reference to FIGS. 6 and 7, once the platform 104 is secured to the anatomy, in an anatomical shoulder procedure, the glenoid component 102 can be coupled to the platform 104. The glenoid component 102 can be coupled to the platform 104 such that the tab 112 engages the groove 126 and a bottom surface 110*a* of the augment 110 rests against the lip 128. In order to perform a reverse shoulder procedure, the glenoid component 102 can be removed from the platform 104. Then, the glenosphere 18 can be coupled to the platform 104 via the locking of the tapered stem 86 to the tapered region 68.

Accordingly, the modular glenoid prosthesis 10, 100 can be used to repair damaged tissue in the anatomy, such as repairing a glenohumeral joint. By using a single platform 14, 104 in an anatomical shoulder procedure, a reverse shoulder procedure can be later performed with reduced bone removal and surgical time, thereby improving patient recovery. Further, the use of a single platform 104 with augments 110 can enable the single platform 104 to be used with differently sized glenoid components 102, providing a surgeon with a variety of options to suit the needs of various patients.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A modular glenoid prosthesis for replacing a portion of an anatomy, comprising:
    a platform having a coupling portion, a base and a central bore that extends from the coupling portion through the base and defines a tapered region, the coupling portion including a plurality of bores and a groove coupling feature on a side surface of the platform;
    a glenoid component having at least one augment extending therefrom and including a tab configured to engage the groove coupling feature of the platform, and a plurality of pegs, each of the plurality of pegs couplable to a respective one of the plurality of bores; and
    a glenosphere including a tapered stem couplable to the tapered region,
    wherein the glenoid component and the glenosphere are selectively couplable to the platform for replacing the portion of the anatomy.

2. The prosthesis of claim 1, wherein the glenoid component includes a first arcuate side opposite a second arcuate side and a first planar side opposite a second planar side.

3. The prosthesis of claim 2, wherein the at least one augment is formed adjacent to at least one of the first planar side and the second planar side.

4. The prosthesis of claim 1, wherein the glenoid component comprises a polymer and the at least one augment comprises metal.

5. The prosthesis of claim 4, wherein the at least one augment is molded into the glenoid component.

6. The prosthesis of claim 1, wherein the groove coupling feature engages the tab and supports the at least one augment.

7. The prosthesis of claim 6, wherein the platform has at least one lip that contacts a surface of the at least one augment to support the at least one augment on the platform.

8. The prosthesis of claim 1, wherein the plurality of bores of the platform comprises four bores, and the plurality of pegs of the glenoid component comprises four pegs, each of the pegs configured to snap fit into a respective one of the four bores of the platform.

9. The prosthesis of claim 1, wherein a relief cut-out is defined adjacent to at least one of the plurality of pegs to facilitate the removal of the glenoid component from the platform.

10. The prosthesis of claim 1, wherein the platform has a first arcuate side opposite a second arcuate side and a first planar side opposite a second planar side.

11. A modular glenoid prosthesis for replacing a portion of an anatomy, comprising:
 a platform having a plurality of sides, a coupling portion and a central bore defining a tapered region, the coupling portion including a plurality of bores, at least one of the plurality of sides including a coupling feature defining a groove; and
 a glenoid component having a plurality of pegs and at least one augment including a tab configured to be received in the groove and engage the platform, each of the plurality of pegs couplable to a respective one of the plurality of bores so that the at least one augment engages the coupling feature,
 wherein the at least one augment is formed on the glenoid component such that when the glenoid component is coupled to the platform, at least a portion of the augment extends at or below an uppermost coupling surface of the platform.

12. The prosthesis of claim 11, wherein the platform has a first arcuate side opposite a second arcuate side and a first planar side opposite a second planar side.

13. The prosthesis of claim 12, wherein at least one of the first planar side and the second planar side includes the coupling feature.

14. The prosthesis of claim 13, wherein the coupling feature includes a lip that contacts a bottom surface of the at least one augment to support the at least one augment.

15. The prosthesis of claim 11, further comprising a taper plug receivable within the central bore.

16. The prosthesis of claim 11, provided as a surgical kit and further comprising a glenosphere having a tapered stem, the tapered stem couplable to the tapered region n to secure the glenosphere to the platform.

* * * * *

UNITED STATES PATENT AND TRADEMARK OFFICE
CERTIFICATE OF CORRECTION

PATENT NO. : 8,721,728 B2  
APPLICATION NO. : 13/447627  
DATED : May 13, 2014  
INVENTOR(S) : Nathan A. Winslow et al.

It is certified that error appears in the above-identified patent and that said Letters Patent is hereby corrected as shown below:

Title Page, item (57)
Column 2, Abstract, Line 8-10, Delete "a plurality of pegs. Each of the plurality of pegs in combination with at least one tab, the tab configured to engage the groove coupling feature of the platform can be" and insert --a plurality of pegs in combination with at least one tab, the tab configured to engage the groove coupling feature of the platform. Each of the plurality of pegs can be--

In the Claims
Column 12, Claim 16, Line 20, after "region", delete "n"

Signed and Sealed this  
Thirtieth Day of December, 2014

Michelle K. Lee  
*Deputy Director of the United States Patent and Trademark Office*